United States Patent [19]

Mequignon

[11] Patent Number: 4,788,533
[45] Date of Patent: Nov. 29, 1988

[54] DEVICE FOR INTERRUPTING THE SNORING OF A SLEEPING PERSON

[76] Inventor: Jean Claude Mequignon, 10 rue Honore de Balzac, 24120 Terrasson la Villedieu, France

[21] Appl. No.: 759,289

[22] Filed: Jul. 26, 1985

[30] Foreign Application Priority Data

Jul. 27, 1984 [FR] France ................................ 84 12115

[51] Int. Cl.$^4$ ............................................. G08B 23/00
[52] U.S. Cl. ....................................... 340/575; 600/28
[58] Field of Search ...................... 340/575, 407, 573; 128/1 R, 905, 716, 721, 132 R

[56] References Cited

U.S. PATENT DOCUMENTS

| | | | |
|---|---|---|---|
| 3,089,130 | 5/1963 | Wilson | 340/407 X |
| 3,480,010 | 11/1969 | Crossley | 128/132 R |
| 3,696,377 | 10/1972 | Wall | 340/575 |
| 3,998,209 | 12/1976 | Macvaugh | 128/1 R |
| 4,220,142 | 9/1980 | Rosen et al. | 340/575 X |
| 4,644,330 | 2/1987 | Dowling | 340/575 |

OTHER PUBLICATIONS

Mountain West Alarm Supply Company, Catalog 1974, p. 47, Attention Getting "Sonalert".

*Primary Examiner*—Glen R. Swanns, III
*Assistant Examiner*—Thomas J. Mullen, Jr.
*Attorney, Agent, or Firm*—Kerkam, Stowell, Kondracki & Clarke

[57] ABSTRACT

A device is provided for interrupting the snoring of the subject as soon as it starts. Said device comprises a microphone (2) for picking up the noise emitted by the subject, and means (3) for comparing the intensity of the noise picked up by the microphone (2) with a given alarm threshold. It is characterized by the fact that it further comprises means (6) which, should the alarm threshold be exceeded, emit for a given brief time a sound stimulus of an intensity sufficient to be perceived by the subject but insufficient to awaken him.

8 Claims, 1 Drawing Sheet

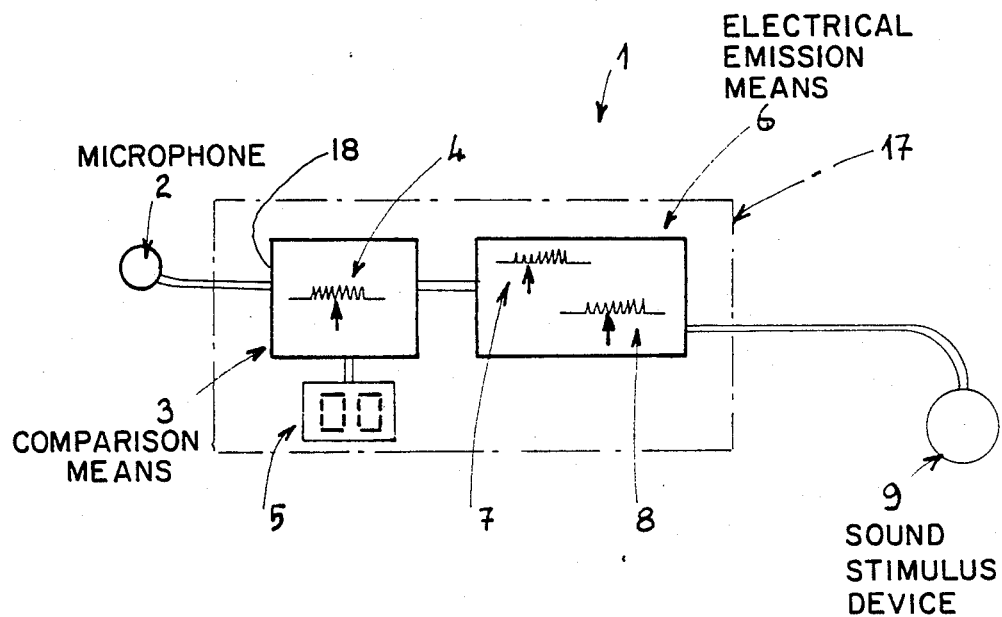
_FIG:1_
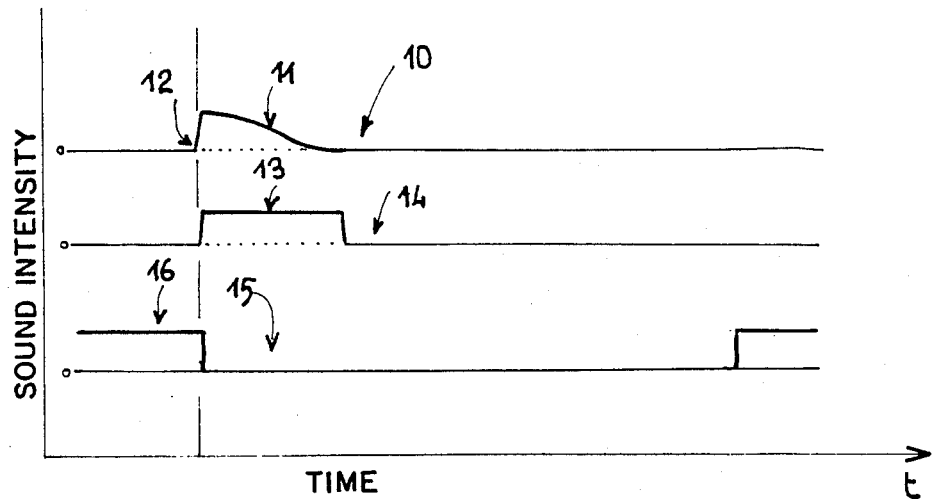
_FIG:2_

DEVICE FOR INTERRUPTING THE SNORING OF A SLEEPING PERSON

The invention relates to a device for interrupting, as soon as it starts, the storing of a sleeping human being. It is known that the snoring of a person is annoying and disagreeable to put up with and harmful for the health.

Devices exist at present whose purpose is to "decondition" a sleeping person having predispositions for snoring. These devices generally react, as soon as snoring begins, so as to establish a relationship between the snoring and a precise phenomenon, very often disagreeable or irritating for the person.

For example, some devices set off an alarm so as to wake the sleeping person, possibly forcing him to get up or subjecting him to a succession of visual, sound or touch senstations whose main purpose is to cause a reaction of irritation in the person.

Devices are known which are described in the U.S. Pat. Nos. 3,998,209 and 4,220,142.

These devices further allow the sleeping person to assess his progress, in particular the second device which comprises means for memorizing over several days.

Such devices are efficient but have the major drawback of profoundly disturbing the sleep of the person and his close relations, which may have repercussions in their behavior outside sleeping hours.

In U.S. Pat. No. 3,396,377 a device is also known which, as soon as the first snoring of the sleeping person begins, causes him to hear a message of a low sound level but long enough to teach him the reflexes necessary for him to get over this habit.

Although it is less annoying for the people close to him, this device is however less efficient than the two preceding devices for it acts indirectly on the subconscious of the sleeping person and does not necessarily cause the sleeper to follow the method taught.

One of the aims of the present invention is to propose a device which reacts as soon as the first snoring of a sleeping person begins and which is really efficient for interrupting the snoring, without however disturbing the sleep of the person, i.e. without wakening him.

Another aim of the present invention is to propose a device which allows the sleeper to know in the morning, when wakening up, the number of times that he has triggered off the system by snoring;

Other aims and advantages of the present invention will be clear from the following description.

The device intended for interrupting the snoring of a human being, as soon as it starts, comprises means such as a microphone for picking up the noise emitted by the subject and means for comparing the intensity of the noise picked up with a predetermined alarm threshold. It is characterized in that it further comprises means which, each time that said alarm threshold is exceeded, emit for a brief predetermined time a sound stimulus of an intensity sufficient for it to be perceived by the subject but insufficient to awaken the snoring person or even those close to him, without troubling his sleep and without disturbing his nightly rest, the progress made by setting up a gentle education-reflex tending to reduce the number and power of the snores.

The invention will be better understood from the following description given by way of non limitative example with reference to the accompanying drawings which show schematically:

FIG. 1: a block diagram illustrating the device of the invention.

FIG. 2: a timing diagram illustrating the action of the device of the invention.

The purpose of the present invention is to interrupt, as soon as it starts, the snoring of a sleeping human being.

The device acts without wakening the subject and it is based on the observation that hearing, on the one hand, is the sense which falls asleep last and, on the other hand, is the sense which sleeps less profoundly during the sleep of a human being.

Thus, during snoring, the device emits a sound stimulus of given frequency, intensity and duration which without wakening him subconsciously causes in the subject a change of behavior resulting in the instantaneous interruption of his snoring.

Referring to FIG. 1, the device 1 of the invention comprises in a way know per se a microphone 2 which is intended to pick up the noises emitted by the subject.

By way of example, good results have been obtained with a microphone of the "Electret" type, made sensitive to about 50/60 dB.

Naturally, any other microphone is suitable and more generally any means for picking up the noises emitted by the subject.

Device 1 further comprises means shown schematically at 3 for comparing the intensity of the noise picked up by microphone 2 with a given alarm threshold.

In a way known per se, these means may also comprise a filtering device, possibly a time delay device or generally any appropriate means for eliminating, apart from a snore, the other noises picked up by microphone 2.

These comparison means 3 further comprise a sensitivity adjustment shown schematically at 4 for adjusting the alarm threshold with which the noise picked up by microphone 2 is compared.

If need be, counting means shown schematically at 5 may count the number of times that the strength of the noise picked up by the microphone exceeds the given alarm threshold, during a given period, for example one night.

These counting means further comprise resetting means and possibly means for memorizing the performance of the preceding days.

It should be mentioned that, in the case of the invention, the counting means play an important role for, not being awakened during his sleep and waking up in the morning the subject has no idea of the number of times that he has triggered off the apparatus.

The counting means are therefore for him the means for assessing, without troubling his sleep and without disturbing his nightly rest, the progress made by setting up a gentle education-reflex tending to reduce the number and power of the snores, contrary to the other existing devices in which the subject is wakened a more or less large number of times during the night.

According to a feature of the invention, device 1 further comprises means which, should the alarm threshold be exceeded, emit an electrical signal for a given brief time which actuates a sound stimulus at a sound level of an intensity sufficient for it to be perceived by the subject and insufficient to waken him. These means 6 come into action under the effect of a signal received from the comparison means 3 corresponding to overshooting of the alarm threshold.

They act for a given brief time which is adjustable by means of a delay shown schematically at 7 and emit a sound stimulus whose intensity is adjustable by the means shown schematically at 8.

Good results have been obtained with a sound stimulus emitted by means 6 whose frequency is of the order of 2000 Hz plus or minus ten per cent and more especially between 1700 and 2300 Hz.

Also, good results have been obtained with a sound stimulus whose intensity is between 50 and 90 dB. Such a sound stimulus may be obtained for example by a vibrator shown schematically at 9 or a buzzer.

The duration of emission of the stimulus from this vibrator 9 is adjusted to a value of the order of 2 to 3 seconds and emission begins substantially as soon as the alarm threshold is exceeded. Naturally, these figures have only indicative value.

Preferably, should the alarm threshold be overshot and a sound stimulus emitted by the vibrator 9, microphone 2 is automatically disconnected for a time greater than the emission of the stimulus by the disconnecting means 18 and the reaction time of the subject. The duration of such a disconnection may be more especially of the order of 5 to 10 seconds. After this period, it is automatically switched back into circuit and the device resumes its monitoring, and may again emit a stimulus by means of vibrator 9 if the snoring has not ceased or if it starts up again.

FIG. 2 shows schematically the operation of this device.

The upper curve 10 and particularly its portion 11 correspond to the snoring of a subject.

As soon as this snoring begins, shown schematically at 12, the vibrator 9 comes into action for a given time shown schematically by the square wave 13 of curve 14.

In addition, the microphone is disconnected for a longer time than the emission time of the stimulus, which is shown schematicaly by the square wave 15 of curve 16.

The sound stimulus emitted by the vibrator whose intensity is sufficient for it to be received by the subject but insufficient to waken him causes a subconscious change of behavior in the subject interrupting his snoring. If however the snoring continues a new stimulus is emitted by the vibrator as soon as microphone 2 is switched back into circuit.

The device of the invention is advantageously constructed in the form of a case shown schematically at 17 which contains the comparison means 3 and the emission means 6.

Microphone 2 may be integrated in this case 17 or else it may be independent and connected by a connecting wire.

Vibrator 9 is preferably independent and it is connected by a wire of sufficient length for placing for example under the pillow or the bolster at the level of the subject's head.

It may also be without wire and be controlled by radio waves or any other means.

The sound intensity of the stimulus emitted by vibrator 9, adjustable by means 8 is adjusted in accordance with the keenness of hearing and/or the depth of sleep of the subject.

Case 17 further comprises appropriate power supply means, not shown, which may be for example a transformed electric power supply from the AC mains or a set of dry cells.

Naturally, the present description is only given by way of example and other embodiments of the invention could be adopted without departing from the scope and spirit thereof. In particular, by way of example, the vibrator could be actuated by controlled radio waves.

The whole of the device, using existing or future means, could be contained integrally in the auditive duct and/or the external ear, etc.

I claim:

1. A device for interrupting the snoring of a sleeping subject as soon as it starts and which uses the phenomena of subconscious perception of a fixed frequency sound wave stimulus to cause a snoring sleeper to react to the sound stimulus which is maintained at a level not loud enough to wake the subject but sufficiently loud to cause a subconscious physical response, the result of which is to cause a behavioral change and interruption of the snoring without waking the subject, said device including a microphone (2) for picking up snoring noise emitted by the subject and means (3) for comparing the intensity of the noise picked up by the microphone (2) with a given alarm threshold, means (6) for disabling the microphone for a predetermined period upon the noise exceeding the alarm threshold and means for actuating a sound device so as to emit a fixed frequency sound stimulus within the range of 1700 and 2300 Hz and of an intensity between 50 db and 90 db such that the sound stimulus is perceived by the subconscious perception of the subject but insufficient to awaken the subject, said sound device being activated for a period between approximately 2 and 3 seconds so that the sound stimulus is emitted for a predetermined period less than the predetermined period of disablement of the microphone.

2. The device according to claim 1, wherein said means (6) comprises a vibrator (9).

3. The device according to claim 1, wherein said means (6) includes means (7) for adjusting the intensity of the sound stimulus emitted between 50 and 90 dB.

4. The device according to claim 1, wherein said means (6) includes means (8) for adjusting the duration of emission of the sound emitted between 2 and 3 seconds after the alarm threshold has been exceeded.

5. The device according to claim 1, wherein said means (6) includes means for disabling the microphone, (2) for a time adjustable between 5 and 10 seconds.

6. The device according to claim 1, wherein the means (6) includes an adjustable delay for controlling the predetermined period of the sound stimulus.

7. The device according to claim 1 wherein said means for disabling including means for automatically reactivating the microphone to cause it to resume its monitoring function.

8. A device for interrupting the snoring of a subject as set forth in claims 2, 3, 4, 5, 15 or 7 wherein the means (6) for disabling the microphone is operative to disable the microphone for a predetermined period of between 5 and 10 seconds upon the noise exceeding the alarm threshold.

* * * * *

UNITED STATES PATENT AND TRADEMARK OFFICE
CERTIFICATE OF CORRECTION

PATENT NO. : 4,788,533

DATED : November 29, 1988

INVENTOR(S) : Jean Claude MEQUIGNON

It is certified that error appears in the above-identified patent and that said Letters Patent is hereby corrected as shown below:

Claim 5, line 2, after "microphone" delete ",".

Claim 8, line 2, delete "15" and insert --6--.

Signed and Sealed this

Thirtieth Day of May, 1989

Attest:

DONALD J. QUIGG

Attesting Officer

Commissioner of Patents and Trademarks